United States Patent [19]
Reiffel

[11] Patent Number: 6,118,848
[45] Date of Patent: Sep. 12, 2000

[54] SYSTEM TO STABILIZE AN IRRADIATED INTERNAL TARGET

[76] Inventor: Leonard Reiffel, 602 Deming Pl., Chicago, Ill. 60614

[21] Appl. No.: 09/225,940

[22] Filed: Jan. 6, 1999

Related U.S. Application Data

[60] Provisional application No. 60/071,334, Jan. 14, 1998.
[51] Int. Cl.[7] .................................................. A61N 5/10
[52] U.S. Cl. ........................... 378/65; 378/162; 378/163; 378/98.5; 600/439
[58] Field of Search ............................. 378/65, 162, 163, 378/98.5; 600/439

[56] References Cited

U.S. PATENT DOCUMENTS 4,945,914  8/1990  Allen .

Primary Examiner—Craig E. Church
Attorney, Agent, or Firm—Don Moyer

[57] ABSTRACT

A stabilizing system, which is especially useful in radiation therapy, has markers located in a body in a set of positions relative to external coordinates, the set of positions having a calibrated spatial relationship with a target volume in the body, the markers being imaged by an imager at subsequent times to produce subsequent imager output signals which are compared by a data processor which generates a control signal which drives an actuator sub-system to move the body to stabilize the target volume relative to the external coordinates, wherein confounding effects of high energy, high intensity radiations which may also be present in the body are overcome by various distinguishing arrangements.

15 Claims, 1 Drawing Sheet

SYSTEM TO STABILIZE AN IRRADIATED INTERNAL TARGET

CROSS REFERENCES TO RELATED APPLICATIONS

This application claims benefit of U.S. Provisional Application No. 60/071,334 filed Jan. 14, 1998.

STATEMENT AS TO RIGHTS TO INVENTIONS MADE UNDER FEDERALLY SPONSORED RESEARCH AND DEVELOPMENT

BACKGROUND OF THE INVENTION

The invention stabilizes a target volume located in a body relative to external coordinates so that an irradiating beam stays on the target volume and alternatively stays away from the target volume, the beam being controlled relative to the external coordinates by a separate control system. The beam irradiating the body can be any energy beam such as particle beams, beams of various wavelengths of electromagnetic radiation, and beams of acoustic energy. The invention has an actuator sub-system which moves the body to counter movements of the target volume within the body with the actuator sub-system being driven by a control signal output from a data processor which processes signals from an imager which is not confounded by the beam irradiating the target volume and which images markers which are located in the body in a calibrated relationship to the target volume.

There are occasions when a process in a body is intended to have an effect only a target volume in the body and the target volume can move within the body such that the process misses the target volume. For example, when a cancerous tumor in a body is being treated with a photon beam, a particle beam or an acoustic beam, or by hyperthermia or cryotherapy and the position of the tumor changes in the body as a result of respiration, blood flow, gastric motions, and other causes, then the treatment can miss the tumor and harm adjacent tissue which otherwise would be protected.

These problems are well known and workers have long been seeking solutions. In order to compensate for motions of a target volume in a body those motions must be measured. The key problem in the cancer therapy case is that those motions must be measured in the presence of the high energy, high intensity photon and particle radiations typically used in cancer therapy. Though marker imaging systems and positioning systems are shown in prior art—such as by Allen in U.S. Pat. No. 4,945,914—there is no suggestion of a solution to this key problem in prior art.

The invention shown here is based on the discovery of apparatus and methods which can image markers located in a body in the presence of the high energy, high intensity radiations in order to generate fast and reliable control signals to drive an actuator sub-system which moves the body to counter motions of a target volume in the body and thus stabilize the position of the target volume relative to external coordinates. This discovery is not suggested in prior art nor in any combinations of prior art and thus there is no suggestion of a system which images markers located in a body and moves the body to stabilize the position of a target volume in the body in prior art nor in any combinations of prior art.

SUMMARY OF THE INVENTION

Objects of this invention comprise requirements listed in the following imperatives. Make a stabilizing system which has markers located in a body in a reference set of positions relative to external coordinates with the reference set of positions having a calibrated spatial relationship with a target volume in the body. Make an imager which images the markers and produces subsequent imager output signals which are functionally related to subsequent sets of positions of the markers relative to external coordinates at subsequent times. Feed the imager output signals to a data processor which compares the subsequent imager output signals and generates a control signal. Make an actuator sub-system which is driven by the control signal to move the body to counter the motion of the target volume and thus stabilize the position of the target volume relative to the external coordinates.

Other objects of various alternative forms of the invention comprise requirements listed in the following imperatives. Use x-radiation to image the markers. Give the imager two x-ray sources and two x-ray imagers with the outputs from the two x-ray imagers together comprising the imager output signal. Choose x-ray sources and x-ray imagers which are not harmed by high energy, high intensity radiations. Choose x-ray sources and x-ray imagers so that imaged distances between markers are magnified by the imager. Choose x-ray sources and x-ray imagers so that the x-ray imagers are most sensitive to energies of the x-ray sources. Choose materials for markers so that the markers provide greatest contrast at the energy where the imager is most sensitive. Modulate the x-radiation by alternatively passing the x-radiation through filters with different x-ray absorption edges so that parts of images with greatest contrast change between the filters are the markers. Pulse the system so that the system is active between pulses of other radiations present. Have the data processor also generate a supplementary control signal for a control system which controls a process in the body. Make the imager an acoustic imager. Use images of the markers to improve images of the target volume. Make the actuator sub-system a topical actuator with only one degree of freedom.

Other objects will be comprehended in the drawings and detailed description, which will make additional objects obvious hereafter to persons skilled in the art.

In summary one embodiment of this invention has markers located in a body, the markers having a reference set of positions relative to external coordinates, the reference set of positions having a calibrated spatial relationship with a target volume in the body; has an imager which at subsequent times images the markers and produces subsequent imager output signals functionally related to subsequent sets of positions of the markers relative to the external coordinates at the subsequent times; has a data processor which compares subsequent imager output signals and generates control signals; and has an actuator sub-system which is driven by the control signals to move the body to counter motions of the target volume and thus stabilize the target volume relative to the external coordinates.

Other equivalent embodiments will be comprehended in the drawings and detailed description, which will make additional equivalent embodiments obvious hereafter to persons skilled in the art.

DESCRIPTION OF THE PREFERRED EMBODIMENTS

Figure 1:
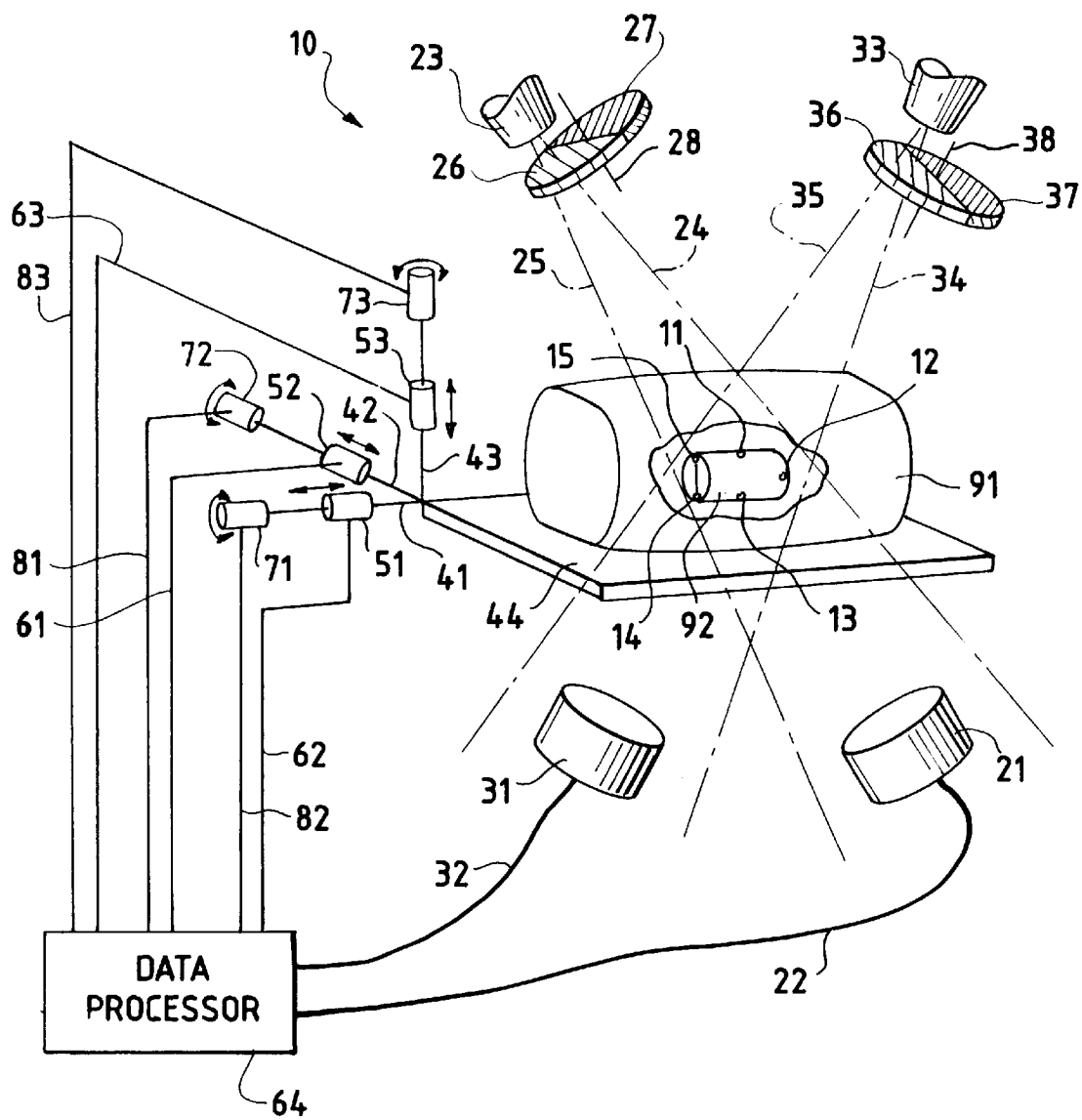
FIG. 1 shows the stabilizing system schematically.

The stabilizing system 10 shown in FIG. 1 comprises a plurality of markers located in a body, an imager which produces an imager output signal, a data processor, and an actuator sub-system. Representative markers comprise a first granular marker 11, a second granular marker 12, a third granular marker 13, and a fourth rod marker having a first end 14 and a second end 15 which are shown in a body 91 in a spatial relation to a target volume 92 in the body. The material, size, and shape of the markers are chosen to provide contrast for the imager. The markers can be implanted in bodies for example by modified biopsy methods and by other implanting methods.

The imager example shown uses x-radiation to image the markers and produce the imager output signal. Specifically, this imager example has a first x-ray source 23 which produces a first beam of x-radiation indicated by a first beam left vector 24 along the first beam left edge and a first beam right vector 25 along the first beam right edge. The first beam passes through markers to a first x-ray imager 21 which sends a first imager output signal 22 to a data processor 64. This imager example also has a second x-ray source 33 which sends a second beam of x-radiation indicated by a second beam left vector 34 along the second beam left edge and a second beam right vector 35 along the second beam right edge. The second beam passes through the markers to a second x-ray imager 31 which sends a second imager output signal 32 to the data processor 64. The first x-ray imager output signal and the second x-ray imager output signal together comprise the imager output signal. Since this imager output signal has components from views of the markers from two different angles the data processor 64 can calculate sets of positions of the markers relative to external coordinates with three orthogonal space dimensions. An equivalent imager could use only one x-ray source and x-ray imager and image the markers from two positions.

The imager images the initial set of positions of the markers at an initial time and produces an initial imager output signal. Then, the imager images a subsequent set of positions of the markers at a subsequent time and produces a subsequent imager output signal. The data processor 64 receives the initial imager output signal and receives the subsequent imager output signal, compares the initial imager output signal with the subsequent imager output signal and produces a control signal which is sent to the actuator sub-system to drive the actuator sub-system to move the body to counter motion of the target volume between the initial time and the subsequent time thus stabilizing the target volume relative to the external coordinates.

The data processor 64 sends a control signal having several components to an actuator sub-system, which, in the example shown, has three orthogonal linear actuators and three orthogonal rotational actuators. Specifically, the example of the control signal shown has a component 61 which drives an actuator 52 which provides linear motion of an x-axis connector 42 connected to a platform 44 which provides motion of the body 91. A control signal component 81 drives an actuator 72 which provides rotational motion to the x-axis connector. A control signal component 62 drives an actuator 51 which provides linear motion to a y-axis connector 41 connected to the platform 44. A control signal 82 drives an actuator 71 which provides rotational motion to the y-axis connector. A control signal 63 drives an actuator 53 which provides linear motion to a z-axis connector 43 connected to the platform 44. A control signal 83 drives an actuator 73 which provides rotational motion to the z-axis connector.

The key for this invention is that imagers can be chosen so that an imager will not be confounded by other radiation present. For example, when the imagers 21 and 31 are micro channel imagers, the x-ray sources 23 and 33 are micro focus x-ray sources, and the markers are gold spheres, then the imager has several properties which overcome difficulties posed by other radiations present. These imagers are designed to be unharmed by high energy, high intensity photon and particle radiations. The x-ray sources and x-ray imagers can be located where they are only effected by scattered radiations. The beam vector pairs—24, 25 and 34, 35—originate from spots as small as 10 microns so that distances between the markers, can be magnified by a factor as large as five and larger. This, combined with the high contrast provided by the gold and the fine resolution of the micro channel imagers, yields high resolution images which can be distinguished from images formed by other radiation from the markers. Also these source and imager pairs afford several further opportunities for overcoming confounding effects due to other radiation present in order to obtain reliable images.

An imager, for example using the micro channel imagers, can be made to be more responsive to the energy of the radiation used, for example from the micro focus x-ray sources, than to other radiations present. Markers can be chosen to have a contrast peak at the energy where the imager is most responsive. The stabilizing system can be pulsed, for example by pulsing the micro focus x-ray source and micro channel imager pairs so that the imager is active only when a pulse of radiation from its source is present. The source-imager pairs can be pulsed at the same frequency and at different frequencies. These pulse frequencies can be arranged so that the source imager pairs are active only between pulses of other radiations present. The stabilizing system can also be pulsed by having the data processor sample the imager output signals only between pulses the other radiations.

The x-radiation used to image the markers can be modulated by having the x-radiation alternatively pass through filters with different x-radiation absorption edges near an x-radiation absorption edge of the markers. Then, parts of the images produced which have the highest contrast change from filter to filter are images of the markers produced by the imaging radiation and thus can be distinguished from any images of the markers produced by stray radiations from other sources.

In the example shown, in front of the first x-ray source 23 there is a first filter 26 and a second filter 27 which rotate about a first axis 28, and in front of the second x-ray source 33 there is a third filter 36 and a fourth filter 37 which can rotate about a second axis 38. Typically the first filter has an x-ray absorption edge at an energy just below the energy of an x-ray absorption edge of the markers and the second filter has an x-ray absorption edge at an energy just above the energy of the x-ray absorption edge of the markers.

The absorption edges of the third and fourth filters can be the same as the absorption edges of the first and the second filters and they can all be different. Similarly, the rotational frequencies about the first and second axes can be the same and they can be different. Various filtering modulations can produce the same effect. Other x-radiation modulation examples are a filter to no filter modulation and a first filter to second filter to no filter modulation.

There is now shown a whole menu of distinguishing arrangements which allow the markers to be imaged in the presence of other radiations which otherwise would confound the images. This solves the key problem which heretofore made it impossible to use internal markers in a stabilizing system. Now an imager can image markers and provide an imager output signal so that a data processor can distinguish reliable images of the markers in order to compare subsequent images of sets of positions of the markers and generate control signals to drive an actuator sub-system to move the body and stabilize the target volume relative to external coordinates.

In order to establish a reference set of positions of the markers relative to external coordinates, the positions of the markers relative to the target volume must be calibrated. This can be done by doing a CT scan of the body to show the target volume and the markers relative to the external coordinates. Because of small motions during the duration of the CT scan, the CT image of the target volume and the markers will be blurred somewhat. Since the markers have known sizes and shapes, motions which caused the blur can be calculated from the images. This result can then be used to reduce the blur in the image of the target volume. Thus, the markers located in the body provide data which can be used to improve other imaging technologies.

The calibration establishes a reference set of positions of the markers relative to external coordinates and establishes the spatial relationship of the reference set of positions of the markers to the target volume. (The external coordinates can be the coordinates of the actuator sub-system such as the coordinates defined by the connectors 41, 42, 43.) Thus, when the imager images the set of positions of the markers at some initial time, the initial imager output signal will be functionally related to the reference set of positions (providing that the spatial relationship of the reference set of positions of the markers to the target volume has not changed in the time between the calibration and the initial time). This initial imager output signal can be used to control the initial alignment of a process in the body such as radiation therapy aimed at the target volume.

The data processor compares the initial imager output signal with a subsequent imager output signal generates a control signal. In the time between the initial imager output signal and the subsequent imager output signal the initial set of positions of the markers may have been translated, with components of the translation along three orthogonal axes. The initial set of positions also may have been rotated, with components of the rotation about the three orthogonal axes. And, the initial set of positions may have undergone a strain motion, with components of the strain along the three orthogonal axes.

In the case of the translation and rotation, the control signal can drive the actuator sub-system to move the body to counter the translation and rotation to stabilize the target volume relative to external coordinates. The data processor can also generate an supplementary control signal (not shown) for a seperate control system (not shown) to control a process in the body, for example, to re-orient a beam of therapeutic radiation to stay on the target volume. This supplementary control signal could also be used to re-shape the beam to match a new profile of the moved target volume. When the translation and rotation motions are repetitive motions, such as motions caused by respiration, the supplementary control signal can be used to pulse the therapeutic beam so that the therapeutic beam is on only when the target volume is in its desired position.

When the motion of the target volume in the body has a strain component, then the markers are moving relative to each other. In this case the actuator can not counter the strain motion. Here the data processor can calculate a best fit to the relative motions (perhaps also utilizing information about the properties of the body and the target volume) to generate a supplementary control signal which can be used to re-shape the therapeutic beam to counter the strain motion and keep it on target. The data processor and the control system can be programmed to generate combinations of motions of the body, reorientations of the therapeutic beam, re-shapings of the therapeutic beam, and pulsings of the therapeutic beam to best stabilize the target volume relative to the therapeutic beam and best keep the therapeutic beam on the target volume.

The actuator sub-system is shown as a platform 44 which supports the body and can counter three orthogonal components of translation and three orthogonal components of rotation. The actuators are shown oriented in a Cartesian coordinate system, but other coordinate systems can be utilized to take advantage of any symmetries of the body and of likely motions of the target volume in the body. These symmetries can lead to simplifications of the actuator sub-system. For example, the only troublesome motion of the target volume can be a repetitive motion with only one component of translation along only one axis or only one component of rotation about only one axis. In this case the actuator sub-system can be simplified to a topical actuator which has only one degree of freedom to move the body and is connected to the body at an appropriate location to counter the one dimensional translation or one dimensional rotation.

An imager using x-radiation to image the markers is preferred because very high resolution images can be obtained and because of the menu of distinguishing arrangements which can be used to distinguish the wanted images from images produced by stray radiations. Other portions of the spectrum of electromagnetic radiations along with analogous distinguishing arrangements can also be used. As well acoustic imaging along with analogous distinguishing arrangements can be used. Although acoustic imaging alone can provide a direct image of the target volume the presence of markers (in this case chosen to provide contrast for an acoustic imager) of known sizes and shapes provide reference points more precise than the outlines of a target volume and these can be utilized to improve the acoustic imaging and generate more reliable control signals.

One of the markers shown is in the form of a rod with a first end 14 and a second end 15. This rod marker will not properly track strain motion of the target volume, but, because a rod marker has a known length, one or more rod markers are useful for calibrating imager output signals. A micro thermometer, which is rod-shaped, can be used as a rod marker. This micro thermometer can be read by the imager and provide further information about the target volume.

Other equivalent forms for the markers, the imager, the imager output signals, the distinguishing arrangements, the data processor, the control signal, the supplementary control signal, and the actuator sub-system and other equivalent connections among the elements will be obvious hereafter to persons skilled in the art. Therefore this invention is not limited to the particular examples shown and described here.

I claim:

1. A stabilizing system comprising:
    markers, the markers being located in a body, and the markers having a reference set of positions relative to external coordinates, the reference set of positions having a calibrated spatial relationship to a target volume in the body;
    an imager which images the markers and produces a initial imager output signal which is functionally related to an initial set of positions of the markers relative to the external coordinates at an initial time and produces a subsequent imager output signal which is functionally related to a subsequent set of positions relative to the external coordinates at a subsequent time;

a data processor which receives the initial imager output signal, receives the subsequent imager output signal, compares the initial imager output signal with the subsequent imager output signal, and produces a control output signal;

an actuator sub-system, the actuator sub-system being connected to the body, and the actuator sub-system being driven by the control output signal to move the body.

2. The device of claim 1 wherein the imager uses x-radiation to image the markers.

3. The device of claim 2 wherein the imager comprises:

a first x-ray source which sends a first x-ray beam through the body and through the markers;

a first x-ray imager which receives the first x-ray beam from through the markers;

an initial first imager output signal which is produced by the first x-ray imager at the initial time;

a subsequent first imager output signal which is produced by the first x-ray imager at the subsequent time;

a second x-ray source, which sends a second x-ray beam through the body and through the markers;

a second x-ray imager which receives the second x-ray beam from through the markers;

an initial second imager output signal which is produced by the second x-ray imager at the initial time, the initial second imager output signal and the initial first imager output signal together comprising the initial imager output signal; and a subsequent second imager output signal which is produced by the second x-ray imager at the subsequent time, the subsequent second x-ray imager output signal and the subsequent first x-ray imager output signal together comprising the subsequent imager output signal.

4. The device of claim 2 wherein the x-radiation is modulated by alternatively passing through a filter with a filter x-radiation absorption edge and passing through no filter.

5. The device of claim 2 wherein the x-radiation is modulated by alternatively passing through a first filter with a first filter x-radiation absorption edge and through a second filter with a second filter x-radiation absorption edge.

6. The device of claim 2 wherein the x-radiation is modulated by alternatively passing through a first filter with a first filter x-radiation absorption edge, passing through a second filter with a second filter x-radiation absorption edge, and passing through no filter.

7. The device of claim 1 wherein the imager is more responsive to the radiation used by the imager than to other radiations present.

8. The device of claim 1 wherein the markers have a contrast peak at an energy where the imager is most responsive.

9. The device of claim 1 wherein imaged distances between markers are magnified by the imager.

10. The device of claim 1 wherein the system is pulsed so that the system is active between pulses of radiation not associated with the imager.

11. The device of claim 1 wherein the data processor produces a supplementary control signal for a control system to control a process in the body.

12. The device of claim 1 wherein the imager is an acoustic imager.

13. The device of claim 1 wherein images of the markers are used to improve images of the target volume.

14. The device of claim 1 wherein the actuator sub-system is a topical actuator which has only one degree of freedom to move the body.

15. The device of claim 1 wherein at least one of the markers is a micro thermometer which can be read by the imager.

* * * * *